US007044925B2

(12) United States Patent
Castillo et al.

(10) Patent No.: US 7,044,925 B2
(45) Date of Patent: May 16, 2006

(54) HINGE SYSTEM FOR REGULATING KNEE JOINT FLEXION AND EXTENSION

(75) Inventors: James D. Castillo, Los Alamos, CA (US); Mike Castillo, San Clemente, CA (US); Bernhard Leitner, Trabuco Canyon, CA (US)

(73) Assignee: Innovation Sports, LLC, Foothill Ranch, CA (US)

(*) Notice: Subject to any disclaimer, the term of this patent is extended or adjusted under 35 U.S.C. 154(b) by 32 days.

(21) Appl. No.: 10/727,006

(22) Filed: Dec. 3, 2003

(65) Prior Publication Data

US 2004/0127825 A1    Jul. 1, 2004

Related U.S. Application Data

(60) Provisional application No. 60/437,059, filed on Dec. 30, 2002.

(51) Int. Cl.
*A61F 5/00* (2006.01)
(52) U.S. Cl. .......................................... 602/16; 602/26
(58) Field of Classification Search ................ 602/16, 602/26, 5, 20, 23
See application file for complete search history.

(56) References Cited

U.S. PATENT DOCUMENTS

| 1,081,448 A | 12/1913 | Quayle |
| 1,388,772 A | 8/1921 | Sheehan |
| 1,390,915 A | 9/1921 | Loth |
| 2,531,486 A | 11/1950 | Weber |
| 2,883,982 A | 4/1959 | Rainey |
| 3,030,634 A | 4/1962 | Blair |
| 3,099,448 A | 7/1963 | Salvo |
| 3,387,305 A | 6/1968 | Shafer |
| 3,669,105 A | 6/1972 | Castiglia |

(Continued)

FOREIGN PATENT DOCUMENTS

EP    297766    4/1989

(Continued)

OTHER PUBLICATIONS

"Strength and Motor Task Performance as Effected by the Carbon Titanium Knee Brace in Normal Health Males", by T.K. Inglehart, 1985, Colorado State . . . University Departtment of Physical Education, Fort Collins, Colorado Springs, 1985 pp. 1-12.

*Primary Examiner*—Henry Bennett
*Assistant Examiner*—Shumaya B. Ali
(74) *Attorney, Agent, or Firm*—Stetina Brunda Garred & Brucker (57) ABSTRACT

A hinge system for a knee brace features a flexion-extension regulating device which is adapted to engage an end portion of the knee brace's upper strut. An elongated main slot is formed through the regulating device to provide a fixed boundary for limiting range of motion. A motion limiting member is connected to the regulating device and is further adapted for connection to an end portion of the knee brace's lower strut. The motion limiting member includes a motion limiter that is disposed within the main slot. The motion limiter is caused to move therealong when the upper and lower struts pivot about a user's knee joint. By confining the motion limiter within the fixed boundary formed by the main slot, the hinge system ensures that the user's knee joint flexes and extends within the prescribed range of motion.

21 Claims, 4 Drawing Sheets

U.S. PATENT DOCUMENTS

| | | |
|---|---|---|
| 3,779,654 A | 12/1973 | Horne |
| 3,785,372 A | 1/1974 | Craig |
| 3,817,244 A | 6/1974 | Taylor |
| 3,900,898 A | 8/1975 | Ackerman |
| 3,902,482 A | 9/1975 | Taylor |
| 3,928,872 A | 12/1975 | Johnson |
| 3,958,569 A | 5/1976 | Vosburgh |
| 4,048,991 A | 9/1977 | Marx |
| 4,136,404 A | 1/1979 | Lange |
| 4,169,467 A | 10/1979 | Rabischong et al. |
| 4,237,708 A | 12/1980 | Bremer, Jr. |
| 4,241,730 A | 12/1980 | Helfet |
| 4,271,831 A | 6/1981 | Deibert |
| 4,361,142 A | 11/1982 | Lewis et al. |
| 4,372,298 A | 2/1983 | Lerman |
| 4,381,768 A | 5/1983 | Ericksen et al. |
| D269,379 S | 6/1983 | Bledsoe |
| 4,407,276 A | 10/1983 | Bledsoe |
| 4,428,369 A | 1/1984 | Peckham et al. |
| 4,463,751 A * | 8/1984 | Bledsoe ................. 602/16 |
| 4,487,200 A | 12/1984 | Feanny et al. |
| 4,489,718 A | 12/1984 | Martin |
| 4,493,316 A | 1/1985 | Reed et al. |
| 4,494,534 A | 1/1985 | Hutson |
| 4,503,846 A | 3/1985 | Martin |
| 4,523,585 A * | 6/1985 | Lamb et al. ............. 602/16 |
| 4,554,913 A | 11/1985 | Womack et al. |
| D284,702 S | 7/1986 | Castillo |
| 4,599,998 A | 7/1986 | Castillo |
| 4,603,690 A | 8/1986 | Skeen |
| 4,614,181 A | 9/1986 | Karlsson |
| D286,183 S | 10/1986 | Womack et al. |
| 4,620,532 A | 11/1986 | Houswerth |
| 4,621,624 A | 11/1986 | Rayboy |
| 4,628,916 A | 12/1986 | Lerman et al. |
| 4,665,905 A | 5/1987 | Brown |
| 4,681,097 A | 7/1987 | Pansier |
| D292,529 S | 10/1987 | Saare |
| 4,697,583 A | 10/1987 | Mason et al. |
| 4,699,129 A | 10/1987 | Aaserude et al. |
| 4,715,363 A | 12/1987 | Detty |
| 4,723,539 A | 2/1988 | Townsend |
| 4,753,240 A | 6/1988 | Sparks |
| D298,568 S | 11/1988 | Womack et al. |
| 4,791,916 A | 12/1988 | Paez |
| 4,803,975 A | 2/1989 | Meyers |
| 4,805,606 A | 2/1989 | McDavid, III |
| 4,854,308 A | 8/1989 | Drillio |
| 4,856,501 A | 8/1989 | Castillo et al. |
| 4,886,054 A | 12/1989 | Castillo et al. |
| 4,938,207 A | 7/1990 | Vargo |
| 4,940,044 A | 7/1990 | Castillo |
| 4,955,369 A | 9/1990 | Bledsoe et al. |
| 4,964,402 A | 10/1990 | Grim et al. |
| 4,986,264 A | 1/1991 | Miller |
| D318,736 S | 7/1991 | Castillo |
| 5,063,916 A | 11/1991 | France et al. |
| 5,121,742 A | 6/1992 | Engen |
| 5,135,469 A | 8/1992 | Castillo |
| 5,230,697 A | 7/1993 | Castillo et al. |
| 5,267,946 A | 12/1993 | Singer et al. |
| 5,288,287 A | 2/1994 | Castillo et al. |
| D346,028 S | 4/1994 | Lengyel |
| 5,398,383 A | 3/1995 | Bingold |
| D357,070 S | 4/1995 | Castillo |
| D370,533 S | 6/1996 | Kilbey |
| 5,547,464 A | 8/1996 | Luttrell et al. |
| 5,571,206 A | 11/1996 | Varn |
| 5,743,117 A | 4/1998 | Woo et al. |
| 5,947,916 A | 9/1999 | Riedlinger |
| D416,624 S | 11/1999 | Nauert |
| 5,997,493 A * | 12/1999 | Young .................... 602/16 |
| 6,090,057 A * | 7/2000 | Collins et al. ............ 602/16 |
| 6,210,352 B1 | 4/2001 | Williams et al. |
| 6,464,657 B1 | 10/2002 | Castillo |

FOREIGN PATENT DOCUMENTS

| | | |
|---|---|---|
| FR | 2581859 | 11/1986 |
| FR | 2627381 | 8/1989 |
| GR | 1491569 | 7/1969 |
| GR | 2432766 | 3/1975 |
| WO | WO 84/00533 | 11/1984 |
| WO | WO 9215264 | 3/1992 |

* cited by examiner

HINGE SYSTEM FOR REGULATING KNEE JOINT FLEXION AND EXTENSION

CROSS-REFERENCE TO RELATED APPLICATIONS

The present application claims priority to U.S. Provisional Application Ser. No. 60/437,059 entitled HINGE SYSTEM FOR REGULATING KNEE JOINT FLEXION AND EXTENSION filed Dec. 30, 2002.

STATEMENT RE: FEDERALLY SPONSORED RESEARCH/DEVELOPMENT

BACKGROUND OF THE INVENTION

The present invention relates generally to hinge mechanisms for knee braces, and more particularly to an improved hinge system for a knee brace which is adapted to simulate the movements of a knee joint while regulating its flexion and extension within a plurality of prescribed ranges of motion.

A knee joint is essentially comprised of two joints, namely, lateral and medial joints, which are positioned between the femur and tibia. The primary movements of the knee joint are flexion (rearward rotational movement of the tibia relative to the femur) and extension (forward rotational movement of the tibia relative to the femur). The flexion and extension movements of the knee joint are not, however, limited to simple pivotal movements about a fixed axis.

Rather, the axis around which flexion of the knee joint occurs shifts backward, while shifting forward during extension thereof. This is different from other types of hinge joints such as elbow joints where the axes of rotation do not shift at all.

When the knee joint is fully extended, the tibia is rotated forward which in effect locks the joint in position with the ligaments taut. This tend to provide greater stability to the knee joint. Furthermore, when the knee joint begins to flex from the fully extended position, the tibia first is lowered with a small external rotation which unlocks the knee joint. Thereafter, the tibia rotates rearward about the knee joint to full flexion. In this regard, the initial unlocking of the knee joint during flexion proceeds actual full rotation of the knee.

Because of the complexity associated with knee movement as described above, a knee brace hinge mechanism must be able to simulate the movements of the knee than a simple hinge. The incorporation of such hinge mechanism is important as the knee brace must optimally support the knee joint of its user. For instance, in the context of post-surgical applications, the requirement for such simulation of the knee joint is essential in order to properly rehabilitate and/or prevent re-injury of an injured knee joint. In addition to this requirement for such post-surgical applications, the hinge mechanism should also be able to control the range of knee joint flexion and extension so that the joint does not re-injure itself due to hyper-extension and/or flexion. As the optimal range of knee joint motion may vary between users and/or change during the progress of rehabilitation, the knee brace hinge mechanism used in conjunction with such surgical applications should further be adjustable to correspond to the particular motion range of the user's leg.

In recognizing the need for an effective post-surgical knee brace, various types of hinge mechanisms have been incorporated into currently available knee braces for post-surgical applications. However, most conventional hinge mechanisms typically fail to provide the precise simulation of knee joint movement as described above or control the range of knee joint motion. Such deficiency inevitably decreases the likelihood of the user's knee joint from being properly rehabilitated after surgery. Further, most contemporary knee brace hinge mechanisms typically fail to possess sufficient adjustability so as to quickly and easily provide the optimal set range of knee motion depending upon the current user's needs and/or rehabilitation progress.

In view of the above-described shortcomings of conventional knee brace hinge mechanisms, there exists a substantial need in the art for a hinge system that can closely simulate the motion of the knee joint while regulating the range of its flexion and extension. More specifically, there exists a substantial need for a hinge system which can be easily and quickly adjusted so as to provide a variable, optimal range of knee joint flexion and extension for the particular need of its user.

BRIEF SUMMARY OF THE INVENTION

The present invention specifically addresses and alleviates the above-referenced deficiencies associated with the use of the knee brace hinge mechanisms of the prior art. More particularly, the present invention comprises an improved hinge system for a knee brace which is sized and configured to simulate the movement of a knee joint while regulating its flexion and extension within a plurality of prescribed ranges of motion. The present hinge system's adaptability to simulate and regulate the knee joint movements within a selected optimal range of motion helps to rehabilitate an injured knee joint and may further prevent re-injury of the same due to hyper-extension and/or flexion.

In accordance with a preferred embodiment of the present invention, there is provided a knee brace hinge system adapted to simulate the anatomical movement of a knee joint while regulating its flexion and extension within a plurality of variable prescribed ranges of motion. This hinge system may be incorporated into a variety of knee braces such as sports braces, post-surgical and/or osteoarthritis knee braces.

The system includes a flexion-extension regulating device having an upper member and a lower member that are attached to each other in a manner as to define a gap therebetween. This gap is sized to accommodate an end portion of the knee brace's upper strut whereat fasteners may be used thereafter to fixedly maintain it therewithin. The lower member preferably comprises an outer periphery forming a configuration which corresponds with that of the upper strut's end portion so that the end portion can be fully supported thereon for better accommodation. Although the upper and lower members may be two separate components which are merely attached to each other via fastening, adhering and the like, it is preferred that they are unitarily formed to each other.

In the preferred embodiment of the present invention, an elongated main slot is defined through the upper and lower members. The elongated main slot is formed by substantially aligning the upper member's elongated upper slot and the lower member's elongated lower slot together. The main slot provides a fixed boundary which sets a prescribed range of motion allowing for controlled flexion and extension of a user's knee joint.

The elongated main slot is preferably formed in an arcuately curved configuration. In conformance with the curved main slot, the upper member may form a generally arcuate configuration where substantial portions of its outer periphery are curved in the same direction as the curvature of the main slot. However, this specific configuration of the upper member is not required but merely preferred as other configurations that are adequate in size to form the curved slot therethrough would suffice.

In accordance with the preferred embodiment of the present invention, there is provided a motion limiting member is pivotally connected to the lower member at its surface which faces away from the upper member. It is further pivotally connected to an end portion of the knee brace's lower strut. An elongated arm member is pivotally attached to the lower strut opposite from the motion limiting member and extends to be further pivotally attached to the upper strut of the knee brace.

By providing such multi-rotational linkage, the motion limiting member allows relative movement of the upper strut and lower strut in a regulated manner about a varying pivot axis. This simulates normal knee joint movement wherein during initial movement of the tibia relative the femur in flexion, the tibia slightly lowers to unlock the knee joint and once unlocked; subsequently pivots rapidly backward in flexion. Of course, the knee joint movement is reversed into extension by the tibia rotating forward which in effect ultimately locks the joint in position with the ligaments taut.

The motion limiting member has a motion limiter which is essentially a projection that extends perpendicularly outward with respect thereto. Such projection preferably comprises a flange fabricated from any rigid material such as metal. When the motion limiting member is attached to the lower member as described above, the outwardly extending motion limiter aligns itself within the main slot.

The motion limiting member preferably is formed having a generally triangular configuration. However, the motion limiting member may be formed in any configuration which allows the motion limiter to be freely disposed within the fixed boundary defined by the main slot. By being freely disposed within the main slot, the motion limiter is allowed to slide between the fixed boundary limits of the arcuate slot when the knee brace's upper and lower struts pivot about the knee joint.

In this respect, the elongated arcuate main slot defines a fixed boundary which facilitates a predetermined range of motion for allowing knee joint flexion and extension. The fixed boundary may be variably sized i.e. lengthened or shortened to yield different ranges of motion. However, it is preferred that such range of motion is between about 0 to 140 degrees, that is, the position formed by the tibia in relation to the femur in terms of degrees.

The prescribed range of motion may be adjusted in two ways. The first manner of adjusting the prescribed range of motion is through the use of at least one stop member. The stop member may be removably placed within the elongated main slot to selectively shorten the length of fixed boundary in which the motion limiter is allowed to move. Further, the use of two stop members is also contemplated as the motion limiter may be confined therebetween, thus limiting its range of motion to the length set by both stop members.

The second manner of adjusting the prescribed range of motion is to utilize two sets of stop members in combination. The first set of stop members comprise multiple members essentially of different lengths to control flexion of the user's knee joint. Likewise, the second set of stop members also comprises multiple members each haling a different length for the purpose of controlling the extension of the user's knee joint. One stop member from each of the sets may be selected (depending upon the length desired) and placed apart from each other at the respective ends of the elongated main slot, which results in the formation of a new prescribed range of motion.

In operation, a knee brace (e.g., sports brace, post-surgical and/or osteoarthritis knee braces) incorporating the present hinge systems is worn upon a leg of a user for the purpose of regulating the flexion and extension of his/her knee joint within an optimal range of motion. Such regulation helps to rehabilitate an injured knee joint and/or prevent re-injury of the same due to hyper-extension and/or flexion. Of course, it is recognized that an additional knee brace may be further worn upon the remaining leg.

When such knee brace is worn upon the user's leg, and more particularly about the knee joint, the knee brace acts to simulate the movements of the knee joint. However, the interaction of the motion limiter and the main slot as discussed above limits the movement of the knee brace's upper and lower struts. This consequently limits the flexion and extension of the user's knee joint within the predetermined range of motion prescribed by the main slot's fixed boundary (preferably between about 0 to about 140 degrees).

If the user wishes to adjust the range of motion of his or her knee joint, stop member(s) may be applied to each of the hinge system. As noted above, the stop member(s) may be placed within the main slot to selectively adjust the fixed boundary in which the motion limiter is allowed to travel. Essentially, the stop member(s) is used to shorten the fixed boundary so that the range of motion can be set at less than 140 degrees, and may be done so in 5 to 10 degree increments, or lower if desired.

BRIEF DESCRIPTION OF THE DRAWINGS

These as well as other features of the present invention will become more apparent upon reference to the drawings wherein.

DETAILED DESCRIPTION OF THE INVENTION

Figure 1:
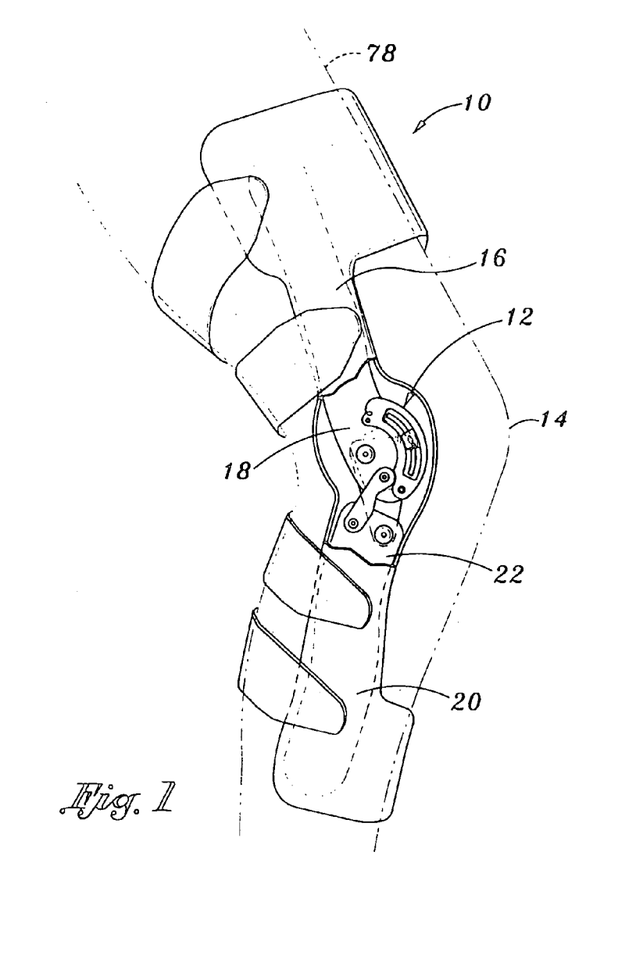
FIG. 1 is a perspective view of a knee brace constructed in accordance with a preferred embodiment of the present invention and illustrating a flexion-extension regulating hinge system which is attached to the end portions of its outward-facing pair of upper and lower struts.

Referring now to the drawings wherein the showings are for purposes of illustrating preferred embodiments of the present invention only, and not for purposes of limiting the same, FIG. 1 illustrates a knee brace 10 constructed in accordance with a preferred embodiment of the present invention. As indicated above, the present knee brace 10 includes a unique hinge system 12 which simulates the movement of a user's knee joint 14, while being capable of regulating its flexion and extension within a number of prescribed ranges of motion. This ability to simulate and regulate the knee joint movements within a selected optimal range of motion helps to rehabilitate an injured knee joint 14 and may further prevent re-injury of the same due to hyper-extension and/or flexion.

Figure 2:
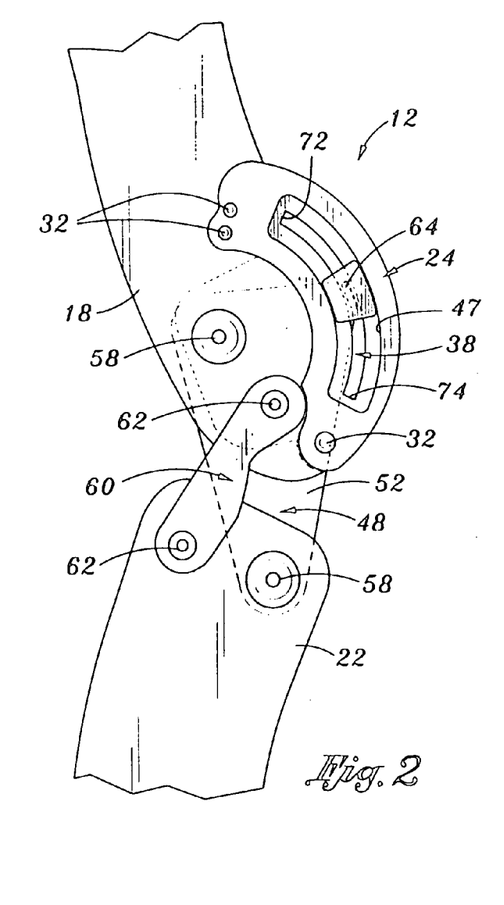
FIG. 2 is an enlarged side view of the flexion-extension regulating hinge system of FIG. 1 and illustrating its elongated, arcuately curved main slot utilized for providing a prescribed range of motion in which a user's knee joint is allowed to flex and extend.
Figure 5:
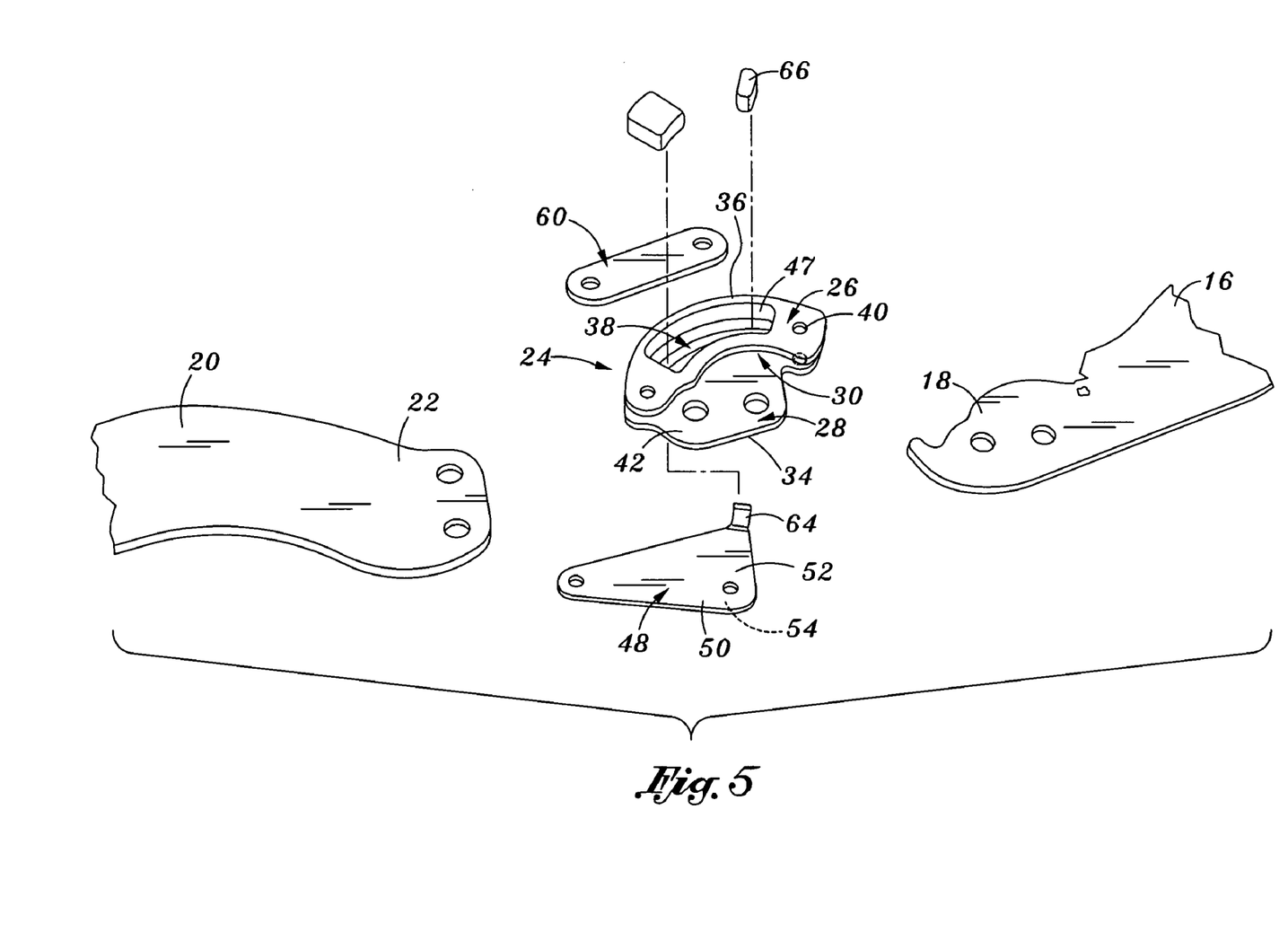
FIG. 5 is a perspective exploded view of the flexion-extension regulating hinge system of FIG. 1 and illustrating stop members which are disposable within the elongated main slot for adjusting the prescribed range of motion.

Referring more particularly to FIGS. 2 and 5, the knee brace hinge system 12 of the present invention may be utilized in conjunction with various knee braces. Types of knee braces that are compatible with the present hinge system 12 are sports braces, post-surgical and/or osteoarthritis knee braces. However, the applicability of the hinge system 12 is in no way limited to such braces. In this regard, the knee brace 10 portrayed in FIG. 1 is merely exemplary to illustrate the application of the hinge system 12 as other types of braces may be utilized in lieu thereof.

The knee brace 10 includes an upper pair of struts 16 each having respective end portions 18 and a lower pair of struts 20 each having their respective end portions 22. The upper pair of struts 16 and lower pair of struts 20 are disposed in an inverted relative orientation, and are placed on opposite sides of the user's knee joint 14. The hinge system 12 is disposed on both sides of the knee joint 14 between the upper strut 16 and the lower strut 20.

As best illustrated in FIG. 5, the present hinge system 12 first includes a flexion-extension regulating device 24. Although such regulating device 24 may be fabricated from any rigid material (e.g., hard plastic), it is preferably made from metal. The flexion-extension regulating device 24 is formed by attaching an upper member 26 and a lower member 28 together. Additionally, the flexion-extension regulating device 24 may also be formed with the upper and lower members 26, 28 being unitarily formed to each other. However, a gap 30 is created between the upper and lower members 26, 28. The gap 30 created between the upper and lower members 26, 28 is sized so that it may accommodate the end portion 18 of the upper strut 16 therewithin. Device fasteners 32 (e.g., rivets, screws, pins and the like) may then be used to securely maintain the end portion 18 of the upper strut 16 within the gap 30.

Although not mandatory, the lower member 28 preferably defines an lower outer periphery 34 which is larger than the upper outer periphery 36 of the upper member 26, and which substantially corresponds to the configuration of the upper strut's end portion 18. By embodying such periphery 34, the lower member 28 may support the end portion 18 of the upper strut 16 thereon in a manner as to contain the end portion's configuration substantially within its periphery 34.

Referring now to FIGS. 2–5, an elongated main slot 38 is formed through the upper and lower members 26, 28. More specifically, the upper member 26 comprises an upper body 40, whereas the lower member 28 comprises a lower body 42. Although the upper and lower bodies 40, 42 may be formed in a variety of sizes, shapes and configurations, it is preferred that the upper body 40 be defined in a generally arcuate configuration and the lower body 42 be defined in a configuration which substantially corresponds with the upper strut's end portion 18. The upper and lower bodies 40, 42 respectively comprises an upper slot 44 and a lower slot 46 which are substantially aligned with each other when the two bodies 40, 42 are attached. The two slots 44, 46 collectively create the elongated main slot 38. The main slot 38 provides an inner slot periphery 47 which in turn provides a fixed arcuate boundary that serves to define a maximum prescribed range of motion for allowing controlled flexion and extension of a user's knee joint 14. As shown in the specified figures, the elongated main slot 38 is preferably formed having arcuately curved configuration.

Figure 3:
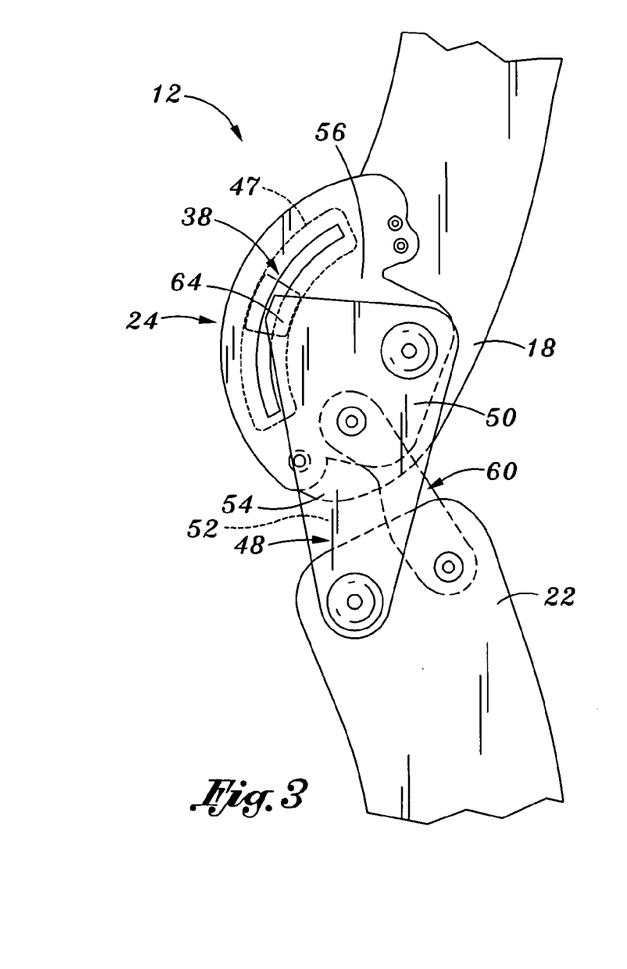
FIG. 3 is an enlarged, opposite side view of the flexion-extension regulating hinge system of FIG. 2 and illustrating a motion limiter which perpendicularly projects outward from its motion limiting member to be aligned within the elongated main slot of FIG. 2.
Figure 4:
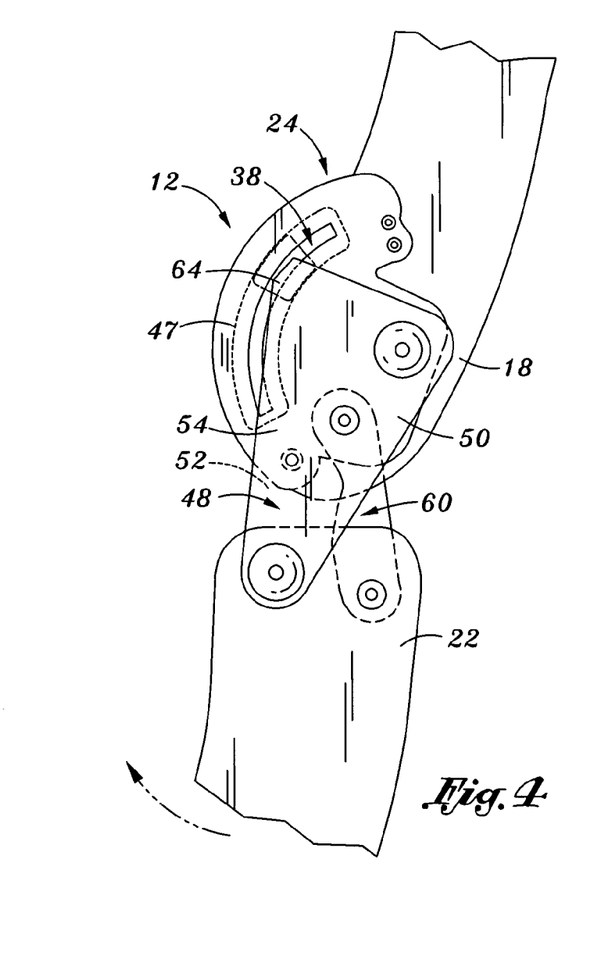
FIG. 4 is an enlarged side view of the flexion-extension regulating hinge system of FIG. 3 and illustrating its motion limiter which is caused to slide along the elongated main slot when the upper and lower struts of the knee brace pivot about the user's knee joint.

FIGS. 3–5 illustrate a motion limiting member 48 having a motion limiting body 50 with a first motion limiting surface 52 and a second motion limiting surface 54. Although the motion limiting member 48 may be constructed from any rigid material (e.g., hard plastic), it is preferably constructed from metal. The first motion limiting surface 52 is pivotally connected to a second lower surface 56 of the lower member 28. Such surface 52 is further pivotally connected to an end portion 22 of the knee brace's lower strut 20. The pivotal connections of the motion limiting member 48 at the second lower surface 56 and the lower strut's end portion 22 may be made through the use of fasteners 58 such as rivets, pins, screws and the like.

Referring now back to FIG. 2, an elongated arm member 60 which can be fabricated from any rigid material, but preferably metal, is additionally provided between the end portions 18, 22 of the upper and lower struts 16, 20 on the opposite side from the attachment of the motion limiting member 48. Such arm member 60 serves to strengthen the connection between the two struts 16, 20 while allowing them to simulate the movements of the user's knee joint 14. The elongated arm member 60 are pivotally attached between the upper and lower struts 16, 20 via fasteners 62 such as pins, rivets, screws and the like.

By forming such multi-rotational linkages by the motion limiting member 48 and the elongated arm member 60, relative movements of the upper strut 16 and lower strut 20 is facilitated about a varying pivot axis. Such movement simulates normal knee joint movement wherein during initial movement of the tibia relative the femur in flexion, the tibia slightly lowers to unlock the knee joint 14 and once unlocked, subsequently pivots rapidly backward in flexion. A more detailed description of the multi-rotational linkage and the manner in which the actual movement of the knee joint is simulated is found in issued U.S. Pat. No. 4,886,054 entitled Knee Brace assigned to the subject Assignee, the disclosure of which is expressly incorporated herein by reference.

A motion limiter 64 is provided on the motion limiting body 50. Preferably, the motion limiter 64 is formed on a corner of the first motion limiting surface 52 which most closely disposed to the elongated main slot 38. This limiter 64 is essentially a projection that extends perpendicularly outwards with respect to the first motion limiting surface 52 towards the elongated main slot 38. Such projection is preferably comprises a flange that may be fabricated from any rigid material. However, metal is preferred due to its strength. The motion limiter 64 is aligned within the elongated main slot 38 when the motion limiting member 48 is attached to the lower member 23 as described above.

The provided figures illustrate the motion limiting member 48 as being formed having generally triangular shape. However, the motion limiting member 48 may be formed in any shape or configuration which allows it to be aligned and freely disposed within the fixed boundary set by the main slot 38. In this respect, the motion limiter 64 slides within the curved, fixed boundary of the elongated main slot 38 when the upper and lower struts 16, 20 of the knee brace 10 is caused to pivot about the user's knee joint 14.

As shown, the elongated main slot 38 accommodates the slidable movement of the motion limiter 64 which is caused by the pivoting action of the struts 16, 20. Because the motion limiter 64 is physically confined within the fixed boundary of the inner slot periphery 47, this limits the movement of the upper and lower struts 16, 20 which in turn further limits the flexing and extending of the user's knee joint 14. As such, the inner slot periphery 47 of the elongated main slot 38 provides a fixed boundary which defines a predetermined range of motion for allowing knee joint flexion and extension. The fixed boundary may vary in size to yield different ranges of motion. However, it is preferred that such range of motion is between about 0 to about 140 degrees, that is, the relative position formed by the tibia in relation to the femur in terms of degrees.

Figure 6:
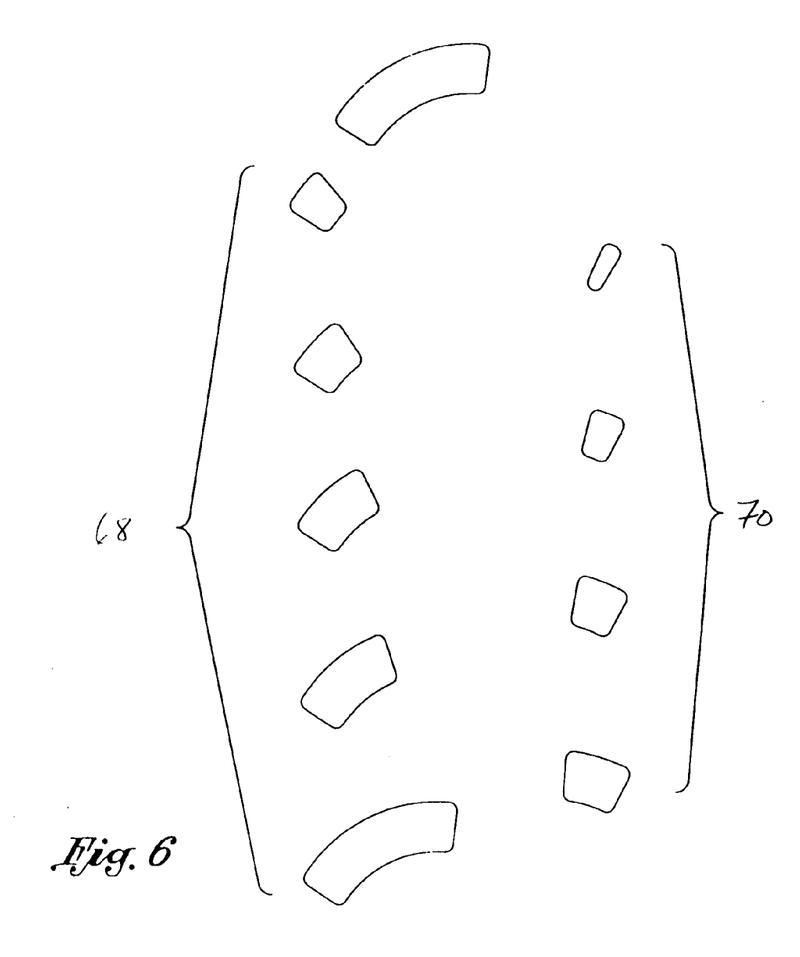
FIG. 6 is a perspective view of two sets of stop members each being comprised of multiple stop members of different lengths which are selectively utilized in combination in the manner shown in FIG. 5 to control flexion and extension of the user's knee joint.

Referring now to FIGS. 5 and 6, the user may manually adjust the prescribed range of motion of the hinge in two ways. The first way of adjusting the prescribed range of motion is through the use of a stop member 66. More particularly, the user may manually and removably position the stop member 66 within the elongated main slot 38 in order to selectively shorten the fixed boundary set by the inner slot periphery 47 in which the motion limiter 64 is allowed to move. In other words, the inner slot periphery 47 of the main slot 38 is shortened to a length desired by the user so that the motion limiter 64 is essentially confined to travel only within the adjusted length of the periphery 47. By utilizing such concept, the use of two stop members 66 is then contemplated herein wherein the motion limiter 64 is confined between the two stop members 66, and therefore allowed to move only along the length of the inner slot periphery 47 which is set between those two stop members 66.

The second way in which the user may manually adjust the prescribed range of motion is to utilize two different sets of stop members 68, 70 in combination. In particular, a first set of stop members 68 is composed of a plurality of different length stop members 66 which are individually used with one other stop member 66 selected from a second set of stop members 70. Likewise to the first set 68, the second set of stop members 70 is also comprised of a plurality of different length stop members 66 which are individually utilized with one other stop member 66 chosen from the first set of stop members 68. By selectively picking out one stop member 66 from each set 68, 70 (depending upon the stop member's length) and placing them in a spaced apart relationship to each other respectively at the two ends 72, 74 of the main slot 38, a new inner slot periphery 47 defining a new prescribed range of motion is created. The use of stop members 66 in this manner effectively controls the flexion and extension of the user's knee joint 14.

Although any number of stop members 66 may form each set 68, 70, it is preferred that the first set 68 (designed for controlling flexion) is comprised of five stop members 66, each defining a body which provides a different length. It is further preferred that the second set 70 (designed for controlling extension) is comprised of four stop members 66, also each defining a body providing a different length. Lastly, an additional lock-out stop member 76 which is used for immobilizing the motion limiter 64 may be provided with the two sets 68, 70. Such stop member 76 would be essentially used for the sole purpose of maintaining the motion limiter 64 in a fixed position so that the user's knee joint 14 is prevented from any movement.

Each of the stop members 66 described above may be fabricated from any rigid or semi-rigid material such as plastic, metal and the like. However, it is preferred that each of the stop members 66 are made from semi-rigid rubber or plastic so that they can be frictionally retained within the inner slot periphery 47 of the main slot 38. Optionally, if the main slot 38 is fabricated in a way as to define a jagged saw tooth inner slot periphery 47, then each of the stop members 66 may accommodate such periphery 47 by having a complementary shaped jagged exterior configuration which corresponds thereto. The indentations formed by the jagged inner slot periphery 47 may then be used to adjust the placement of the stop members in about 5 to 10 degree increments (or in lower increments if desired).

In operation, a knee brace 10 (e.g., post-surgical and/or osteoarthritis knee braces) utilizing the present hinge systems 12 is worn upon a leg 78 of a user for the purpose of regulating the flexion and extension of his/her knee joint 14 within an optimal range of motion. Such regulation helps to rehabilitate an injured knee joint 14 and/or prevent re-injury of the same due to hyper-extension and/or flexion. Of course, it is recognized that an additional knee brace may be further worn upon the remaining leg (not shown).

When such knee brace 10 is worn upon the user's leg 78, and more particularly about his or her knee joint 14, the knee brace 10 acts to simulate the movements of the knee joint 14. However, the interaction of the motion limiter 64 and the elongated main slot 38 as discussed above limits the movement of the knee brace's upper and lower struts 16, 20. This consequently limits the flexion and extension of the user's knee joint 14 within the predetermined range of motion prescribed by the main slot's fixed boundary (preferably between about 0 to about 140 degrees).

If the user wishes to adjust the range of motion of his or her knee joint 14, stop member(s) 66 may be applied to each of the hinge system. As noted above, the stop member(s) 66 may be placed within the elongated main slot 38 to selectively adjust the fixed boundary in which the motion limiter 64 is allowed to travel. The adjustment may be done in small increments, such as by 5 or 10 degrees increments. Essentially, the stop member(s) 66 is used to shorten the inner slot periphery 47 so that the range of motion can be set at less than 140 degrees, and may be done so in 5 to 10 degree increments, or lower if desired.

Additional modifications and improvements of the present invention may also be apparent to those of ordinary skill in the art. Thus, the particular combination of parts described and illustrated herein is intended to represent only certain embodiments of the present invention, and is not intended to serve as limitations of alternative devices within the spirit and scope of the invention.

What is claimed is:

1. A hinge system for a knee brace having upper and lower struts each defining an end portion disposed toward a knee joint, the hinge system comprising:

a flexion-extension regulating device having an upper member and a lower member attached to each other in a manner defining a gap therebetween for accommodating the end portion of the upper strut;

an elongated main slot formed through the upper and lower members and providing a fixed boundary for prescribing a range of motion; and a motion limiting member being pivotally connected to the lower member and further being pivotally connected to the end portion of the lower strut, the motion limiting member having a motion limiter disposed within the main slot which is caused to move thereolong when the upper and lower struts pivot about the knee joint wherein confinement of the motion limiter within the fixed boundary ensures that the knee joint flexes and extends within the prescribed range of motion.

2. The hinge system of claim 1 wherein the knee brace is a post-surgical knee brace.

3. The hinge system of claim 1 wherein the regulating device and the motion limiting member are each fabricated from metal.

4. The hinge system of claim 1 wherein the upper and lower members are unitarily formed to each other.

5. The hinge system of claim 1 wherein the upper member comprises an upper body having a generally arcuate configuration.

6. The hinge system of claim 1 wherein the lower member comprises a lower body having a configuration sized and configured to substantially correspond with the end portion of the upper strut.

7. The hinge system of claim 1 wherein the elongated main slot is curved.

8. The hinge system of claim 1 wherein the upper member comprises an elongated upper slot and the lower member comprises an elongated lower slot, the upper and lower slots being substantially aligned with each other to form the elongated main slot.

9. The hinge system of claim 1 wherein the prescribed range of motion is between about 0 to about 140 degrees.

10. The hinge system of claim 1 wherein the motion limiting member has a motion limiting body with a first motion limiting surface, the motion limiter extending outwardly in a generally perpendicular relationship with respect to the first motion limiting surface.

11. The hinge system of claim 10 wherein the lower member has a lower body with a second lower surface, the first motion limiting surface being connected to the second lower surface in a manner as to align the motion limiter within the elongated main slot.

12. The hinge system of claim 10 wherein the motion limiter is a flange fabricated from metal.

13. The hinge system of claim 1 further comprising at least one stop member removably disposed within the elongated main slot for adjusting the prescribed range of motion.

14. The hinge system of claim 13 wherein the at least one stop member is fabricated from rubber so as to be disposed within the elongated main slot through frictional fit.

15. The hinge system of claim 1 further comprising an elongated arm member sized and configured to be disposed between the end portions of the upper and lower struts.

16. The hinge system of claim 12 wherein the elongated arm member is fabricated from metal.

17. A knee brace for regulating flexion and extension of a knee joint, the knee brace comprising:

an upper pair of struts and a lower pair of struts, the upper pair and the lower pair being placeable in an inverted, relative orientation above and below the knee joint with end portions of the upper pair and the lower pair being disposed laterally on opposite sides of the knee joint; and a pair of hinge systems disposed adjacent the end portions of the upper pair and lower pair to pivot the upper pair and lower pair about the knee joint, each of the hinge systems comprising:

a flexion-extension regulating device engaged to the respective end portion of the upper strut, the device having an elongated main slot formed therethrough and providing a fixed boundary for prescribing a range of motion; and a motion limiting member engaged to the device and being pivotally connected to the end portion of the lower strut, the motion limiting member having a motion limiter disposed within the main slot which is caused to move therealong when the respective upper and lower struts pivot about the knee joint wherein confinement of the motion limiter within the fixed boundary ensures that the knee joint flexes and extends within the prescribed range of motion.

18. The knee brace of claim 17 wherein the knee brace is a post-surgical knee brace.

19. The knee brace of claim 17 wherein the prescribed range of motion is between about 0 to about 140 degrees.

20. The knee brace of claim 17 wherein each of the hinge systems further comprise at least one stop member removably disposed within the elongated main slot for adjusting the prescribed range of motion.

21. The knee brace of claim 17 wherein each of the hinge systems further comprise an elongated arm member sized and configured to be disposed between the end portions of the respective upper and lower struts.

* * * * *